(12) United States Patent
Parker et al.

(10) Patent No.: US 8,007,820 B2
(45) Date of Patent: Aug. 30, 2011

(54) WIDE SPECTRUM INSECTICIDE AND MITICIDE COMPOSITION

(75) Inventors: Diana L. Parker, Brentwood Bay (CA); Cameron D. Wilson, Victoria (CA); George S. Puritch, Saanichton (CA); David S. Almond, Victoria (CA)

(73) Assignee: W. Neudorff GmbH KG, Emmerthal (DE)

( * ) Notice: Subject to any disclaimer, the term of this patent is extended or adjusted under 35 U.S.C. 154(b) by 1317 days.

(21) Appl. No.: 11/531,352

(22) Filed: Sep. 13, 2006

(65) Prior Publication Data
US 2007/0148204 A1    Jun. 28, 2007

Related U.S. Application Data

(60) Provisional application No. 60/718,246, filed on Sep. 16, 2005.

(51) Int. Cl.
*A01N 25/32* (2006.01)
*A01N 43/22* (2006.01)
*A01N 31/02* (2006.01)

(52) U.S. Cl. ......... 424/406; 514/29; 514/557; 514/558; 424/84; 424/405; 424/409; 424/410

(58) Field of Classification Search .................. None
See application file for complete search history.

(56) References Cited

U.S. PATENT DOCUMENTS

| | | | |
|---|---|---|---|
| 4,774,234 A | 9/1988 | Puritch et al. | |
| 4,826,678 A | 5/1989 | Gaudet et al. | |
| 5,093,124 A | 3/1992 | Kulenkampff et al. | |
| 5,362,634 A | 11/1994 | Boeck et al. | |
| 5,437,870 A | 8/1995 | Puritch et al. | |
| 5,631,290 A * | 5/1997 | Almond et al. | 514/560 |
| 5,700,473 A | 12/1997 | Puritch et al. | |
| 6,093,416 A | 7/2000 | Young et al. | |
| 6,352,706 B1 | 3/2002 | Puritch et al. | |
| 6,455,504 B1 * | 9/2002 | Lewer et al. | 514/28 |
| 6,703,036 B1 | 3/2004 | Young et al. | |
| 6,727,228 B2 * | 4/2004 | Janssen et al. | 514/28 |
| 7,530,196 B2 | 5/2009 | Tidow et al. | |
| 7,537,778 B2 | 5/2009 | Parker | |

FOREIGN PATENT DOCUMENTS

| | | |
|---|---|---|
| EP | 1082014 A1 | 3/2001 |
| EP | 1312260 A1 | 5/2003 |
| WO | WO-9933343 A2 | 7/1999 |
| WO | 9960857 A1 | 12/1999 |
| WO | 0112156 A1 | 2/2001 |
| WO | 0170028 A1 | 9/2001 |
| WO | 03024223 A1 | 3/2003 |

OTHER PUBLICATIONS

Thompson, G.D., R. Dutton and T.C. Sparks. 2000. Spinosad—a case study: an example from a natural products discovery program. *Pest Management Science* 56: 696-702.

Cowles, R.S. et al. 2000. Inert formulation ingredients with activity: toxicity of trisiloxane surfactant solutions to twospotted mites. *J. Econ. Entomol.* 93(2): 180-188.

Tjosvold, S.A. and W.E. Chaney. 2001. Evaluation of reduced risk and other biorational miticides on the control of spider mites (*Tetranychus urticae*). *Acta Hort.* 547: 93-96.

Thompson, G.D. et al. 1999. Development of Spinosad and attributes of a new class of insect control products. University of Minnesota IPM Network.

Grossman, J. 1990. Horticultural oils: new summer uses on ornamental plant pests. The IPM Practitioner. vol. XII, No. 8, p. 1.

Canadian Office Action for corresponding Canadian Patent Application Serial No. 2,626,007, dated Jan. 29, 2010, (3 pages).

Thompson, G. D., K. H. Michel, R. C. Yao, J. S. Mynderse, C. T. Mosbert, T. V. Worden, E. H. Chio, T. C. Sparks and S. H. Hutchins. 1997. The discovery of *Saccharopolyspora spinosa* and a new class of insect control products. Down to Earth 52:1-5.

R. S. Cowles, et al. 1998. Effect of Spinosad Formulations and other Miticides on Two Spotted Spider Mite. 1995. Arthropod Manag. Tests 23:342-343.

R. S. Cowles, E. A. Cowles, A. M. McDermott and D. Ramoutar. 2000. Inert formulation ingredients with activity: Toxicity of trisiloxane surfactant solutions to twospotted spider mites (Acari: Tetranychidae). J. Econ. Entomology 93:180-188.

G. D. Thompson, R. Dutton and T. C. Sparks. 2000. Spinosad-a case study: an example from a natural products discovery programme. Pest Management Science 56:696-702.

R. Weinzierl. 2006. Alternatives to pyrethroids for managing corn earworm in sweet corn, seed corn, tomatoes and peppers. Pest Management Network. Jul. 2007, 5 pages.

Material Safety Data Sheet, W. Neudorff GmbH kg, Feb. 9, 2009, 2 pages.

Material Safety Data Sheet, Woodstream Corporation, MDS No. 244, dated Oct. 1, 2002, 2 pages.

Thompson, G. D., K. H. Michel, R. C. Yao, J. S. Mynderse, C. T. Mosbert, T. V. Worden, E. H. Chio, T. C. Sparks and S. H. Hutchins. 1997. The discovery of *Saccharopolyspora spinosa* and a new class of insect control products. Down to Earth 52:1-5.

R. S. Cowles, et al. 1998. Effect of Spinosad Formulations and other Miticides on Two Spotted Spider Mite. 1995. Arthropod Manag. Tests 23:342-343.

R. Weinzierl. 2006. Alternatives to pyrethroids for managing corn earworm in sweet corn, seed corn, tomatoes and peppers. Pest Management Network. Jul. 2007, 5 pages.

Material Safety Data Sheet, W. Neudorff GmbH kg, Feb. 9, 2009, 2 pages.

Material Safety Data Sheet, Woodstream Corporation, MDS No. 244, dated Oct. 1, 2002, 2 pages.

International Search Report WO2007/031565 A3, dated Apr. 18, 2007.

International Search Report WO2007/031561 A3, dated Apr. 17, 2007.

Search Report for WO2007031561 dated Jul. 25, 2007.

* cited by examiner

*Primary Examiner* — Neil Levy
(74) *Attorney, Agent, or Firm* — Nutter McClennen & Fish LLP

(57) ABSTRACT

An environmentally safe, pesticidally effective composition is provided to control insect/mite pests. In an exemplary embodiment, a composition is provided that includes a pesticidally effective, yet environmentally safe, concentration of at least one spinosyn with at least one additional contact-acting insecticide and/or miticide and at least one solvent or carrier.

9 Claims, No Drawings

WIDE SPECTRUM INSECTICIDE AND MITICIDE COMPOSITION

CROSS-REFERENCE TO RELATED APPLICATIONS

This application claims priority to U.S. Provisional Application No. 60/718,246, filed on Sep. 16, 2005, and entitled "Wide Spectrum Insecticide and Molluscicide Composition," the disclosure of which is incorporated by reference herein.

FIELD OF THE INVENTION

The present invention relates to compositions and methods for the treatment of insects and mites, and in particular to compositions and methods that protect plants and plant products from damage caused by a wide spectrum of insect and mite pests.

BACKGROUND

Insect and mite pests cause significant losses to plants and plant products, as well as attack and annoy humans and animals, and affect human and animal health by transmitting disease. It is a major goal for those involved in plant care to control insect and mite pests in ways that protect the environment while, at the same time, are effective in combating a wide spectrum of pests. While several environmentally friendly active compounds have been identified and developed for use in the home and garden markets as well as in commercial agriculture, many of these substances have a narrow range of pest control, and thus require the application of multiple compositions to provide adequate pest control.

Accordingly, there remains a need for an improved composition to treat and prevent insect and mite pests and to protect plants and plant products from damage caused by insect and mite pests.

SUMMARY

The present invention provides various compositions and methods for the treatment of insects and mites, and in particular to compositions and methods that can control pests. In one aspect, an environmentally safe, non-phytotoxic insecticidal and miticidal composition is provided that includes an active amount of at least one spinosyn, at least one of an additional insecticide and miticide, and at least one of a solvent or a carrier. A variety of additional insecticides and miticides can be used with the composition, such as fatty acids, fatty acid salts, fatty acid esters, fatty acid sugar esters, pyrethrum extract, oils, salts of oils, and combinations thereof. The variety of additional insecticides and miticides can also include avermectins.

In one embodiment, the at least one additional insecticide and miticide can be a pyrethrum extract having pyrethins that are selected from the group consisting of pyrethrin I, pyrethrin II, cinerin I, cinerin II, jasmolin I, jasmolin II, and combinations thereof. As noted above, the additional insecticide and miticide can also be an oil that is selected from the group consisting of plant oils, vegetable oils, mineral oils, essential oils, and combinations thereof. In one embodiment, at least a portion of the oil can be a plant oil that is selected from the group consisting of sesame oil, canola oil, cottonseed oil, soybean oil, coconut oil, sunflower oil, safflower oil, rape seed oil, peanut oil, neem oil, olive oil, and mixtures thereof, or an essential oil that is selected from the group consisting of d-limonene, eugenol, cinnamon oil, clove oil, thyme oil, thymol, geraniol, rosemary oil, linalool, mint oil, peppermint oil, citrus oil, garlic oil, pepper oil, and mixtures thereof.

In another embodiment, the additional insecticide and miticide can be a fatty acid having an insecticidally and miticidally effective amount of an active ingredient selected from the group consisting of saturated or unsaturated fatty acids with carbon chain lengths ranging from C8 to C18. Additionally or alternatively, the additional insecticide and miticide can be a fatty acid salt that is selected from the group consisting of potassium, sodium, and ammonium fatty acid salts of saturated or unsaturated fatty acids with carbon chain lengths ranging from C8 to C18, a fatty acid ester that is selected from methyl and ethyl esters of fatty acids with carbon chain lengths ranging from C8 to C18, and/or a fatty acid sugar ester that is selected from the group consisting of sucrose octanoate, sorbitol octanoate, sorbitol decanoate, xylitol decanoate, and xylitol laurate.

As noted above, the composition can also include a solvent. Exemplary solvents can include water, glycerol, propylene glycol, ethanol, isopropyl alcohol, methanol, tetrahydrofurfuryl alcohol, oils, and combinations thereof. The composition can also include a formulation enhancing additive such as preservatives, anti-microbial agents, phagostimulants, waterproofing agents, taste altering additives, and combinations thereof. Additionally or alternatively, the composition can include a carrier, and exemplary carriers can include bait carriers or dust carriers.

In another aspect, a method for controlling insect and mite pests is provided that includes providing a composition that has an effective amount of at least one spinosyn, at least one of an additional insecticide and miticide, and at least one of a solvent or a carrier, and administering an effective amount of the composition to control pests. In one embodiment, where the composition is a liquid, administering an effective amount of the composition can further include at least one of contacting pests, contacting plants and plant products, contacting a vicinity of the pests, and contacting a vicinity of the plants and plant products with an effective amount of the composition. In another embodiment, where the composition is a solid or a dust, and administering an effective amount of the composition can include at least one of placing an effective amount of the composition in a vicinity of pests and placing an effective amount of the composition in a vicinity of plants and plant products to be protected.

DETAILED DESCRIPTION OF THE EXEMPLARY EMBODIMENTS

Certain exemplary embodiments will now be described to provide an overall understanding of the principles of the structure, function, manufacture, and use of the compositions and methods disclosed herein. One or more examples of these embodiments are illustrated in the accompanying tables. Those skilled in the art will understand that the compositions and methods specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides an environmentally safe, and pesticidally effective composition to control pests and/or treat and prevent damage caused by insect and mite pests. In an exemplary embodiment, the composition can include an additional contact-acting insecticide and/or miticide. The compositions can be utilized as liquid concentrates, Ready-To-Use (RTU) liquid sprays, dusts, or solids, depending upon the needs of the user. In use, the composition can be applied to the pests themselves, the vicinity of the pests, and/or the vicinity of plants and plant products that are to be protected.

One skilled the art will appreciate that the compositions and methods disclosed herein can be used to treat a variety of home and garden insect and mite pests such as, by way of non-limiting example, members of the insect order Lepidoptera including Southern armyworm, codling moth, cutworms, clothes moths, Indian meal moth, leaf rollers, corn earworm, cotton bollworm (also called Tomato fruit worm), European corn borer, imported cabbageworm, cabbage looper, pink bollworm, American bolloworm, tomato hornworm, bagworms, Eastern tent caterpillar, sod webworm, diamondback moth, tomato pinworm, grape berry moth, cotton leafworm, beet armyworm, and fall armyworm; members of the order Homoptera including cotton aphid leafhoppers, plant hoppers, pear psylla, scale insects, whiteflies, and spittle bugs; and members of the insect order Diptera including house flies, stable flies, blow flies and mosquitoes; mites; and ants. The composition can also be used to treat members of the order Thysanoptera including melon thrips and Western flower thrips; members of the order Coleoptera, including Colorado potato beetles; members of the order Orthoptera; and Leaf miners of the orders Lepidoptera (moths and butterflies), Hymenoptera (leaf mining sawflies), Coleoptera (beetles), and Diptera (true flies). In the exemplary embodiments, shown in Examples 1-8 below, the composition can be used to control and/or treat ants, green peach aphids, adult house flies, western tent caterpillar larvae, and twospotted spider mites.

As noted above, in one embodiment, the composition includes at least one spinosyn with at least one additional insecticide and/or miticide in a liquid concentrate, RTU liquid spray, dust, or solid form. The spinosyns are macrolides that contain a tetracyclic ring system to which two different sugars are attached. In one embodiment, the spinosyn is isolated from the pesticidal fraction from the soil bacteria *Saccharopolyspora spinosa*, coded A83543. While the spinosyns can be isolated using a fermentation process, they are also commercially available under the brand names Conserve™ SC, SpinTor™, and Entrust™ (all from Dow AgroSciences LLC of 9330 Zionsville Road Indianapolis, Ind. 46268), Fire Ant Nightmare™ from Monterey Lawn and Garden Products, Inc. of P.O. Box 35000 Fresno, Calif., 93745-5000, and Bulls-Eye™ Bioinsecticide from Gardens-Alive! of 5100 Schenley Place, Lawrenceburg, Ind. 47025.

While an exemplary composition includes at least one spinosyn, the composition can also include other spinosyns. For example, the spinosyn can be spinosad, which is a mixture of two of the most active naturally occurring metabolites (spinosyns A and D). Spinosad, as used with the present invention, can be obtained from the commercially available product Entrust™ from Dow, as noted above. Spinosad is a secondary metabolite from the aerobic fermentation of *S. spinosa* on nutrient media. Following fermentation, spinosad can be extracted and processed to form a highly concentrated conventional aqueous suspension for ease of use and distribution. Spinosad is a light gray to white crystalline solid with an earthy odor similar to slightly stale water. It has a pH of about 7.74, is stable to metal and metal ions for about 28 days, and has a shelf life of about three years as formulated material. It is also considered nonvolatile, and has vapor pressures around $10^{10}$ mm Hg. Spinosad is particularly advantageous in that it acts as both a contact and ingested toxin and it excites the insect nervous system, leading to involuntary muscle contractions, prostration with tremors, and paralysis. Spinosad also has effects on GABA receptor functions that may further contribute to its insecticidal activity. As a result, spinosad is effective in combination with insecticidally active ingredients that affect the photochemistry of insect membranes, such as the fatty acid family (e.g., fatty acids, fatty acid esters, and fatty acid salts), and insecticides that provide excellent contact kill and maintain their adherence on the lipophylic surface of insects or plant leaves, such as oils (e.g., plant or mineral oils), as will be discussed in more detail below.

Regardless of the form in which the composition is presented, that is, a liquid concentrate, a RTU liquid spray, a dust, or a solid, it should include an amount of spinosyn that is effective to treat the particular insect or mite pest. In an exemplary embodiment, the end use concentration of spinosyn can be in the range of about 1 ppm to 20,000 ppm, more preferably in the range of about 10 ppm to 4,000 ppm, and most preferably in the range of about 50 ppm to 1,000 ppm. Moreover, the pH of the applied composition can be adjusted to be acidic, alkaline, or neutral, depending upon the particular needs of the user.

The composition can include other active ingredients and/or plant or plant product treatment compounds. In an exemplary embodiment, the composition can include a contact-acting insecticide and/or miticide. Exemplary contact-acting insecticides and/or miticides include those derived from fatty acids, fatty acid esters, fatty acid sugar esters, and fatty acid salts, pyrethrum extract, plant oils and their salts, vegetable oils and their salts, essential oils, mineral oils, pyrethrum extract, and combinations thereof. The contact-acting insecticide and/or miticide can also include avermectins. One skilled in the art will appreciate that the resulting spinosyn-containing compositions disclosed herein are not only pesticidally effective, but also environmentally sound and safe for human use. Further, some of the compositions can be residual in that they do not leach out of baits or easily wash off of the leaves during rain, and thus can protect against insect and mite pests during and after rainy weather. In other embodiments, the compositions can exhibit synergy, and result in better than expected results than just the spinosyn or the insecticide or miticide treatment alone. This can be shown in Examples 4 and 8, which are discussed below.

In one embodiment, the composition can include an active amount of at least one spinosyn, at least one of an additional insecticide and miticide, and at least one solvent. While the composition can be a liquid concentrate, a RTU liquid spray, a dust, or a solid, in an exemplary embodiment, it can be a liquid concentrate or a RTU liquid spray. The at least one additional insecticide and/or miticide can be selected from a variety of compounds, such as fatty acids, fatty acid esters, fatty acid sugar esters, and fatty acid salts, pyrethrum extract, plant oils and their salts, vegetable oils and their salts, essential oils, mineral oils, pyrethrum extract, avermectins, and combinations thereof depending upon the needs of the user. Exemplary additional insecticides and/or miticides can be toxic to soft-bodied insects and mites and, in one embodiment, the at least one additional insecticide and/or miticide can be a fatty acid-based insecticide that includes effective amounts of fatty acids (both saturated and unsaturated) having from 8 to 18 carbon atoms. Exemplary fatty acid salt-based insecticides can include salts of such fatty acids and exemplary fatty acid ester-based insecticides can include sugar esters of such fatty acids. In one embodiment, the fatty aid ester can be selected from methyl and ethyl esters of fatty acids with carbon chains ranging from C8 to C18. While the fatty acid can be present in the composition in a variety of concentrations, in an exemplary embodiment, it can be present at an end use concentration in the range of about 0.05 percent by weight to 2.0 percent by weight.

The at least one additional insecticide and/or miticide can also be a fatty acid salt-based insecticide and/or miticide, and exemplary salts include the potassium, sodium, and ammonium salts of saturated and unsaturated fatty acids having 8 to 18 carbon atoms. By way of non-limiting example, the fatty acid salt can be commercially available under a variety of brand names including Safer's Insecticidal Soap™ from Woodstream, P.O. Box 327, Lititz, Pa. 17543-0327, and Neudosan™ from Neudorff GmbH KG, An der Mühle 3, 31860, Emmerthal, Germany. The fatty acids can also be esterified with sugars or polyols and exemplary esters include sucrose octanoate, sorbitol octanoate, sorbitol decanoate, xylitol decanoate, or xylitol laurate. Other exemplary fatty acid derived pesticidal compositions that can be used with the compositions of the present invention are disclosed in U.S. Pat. Nos. 4,774,234, 4,826,678, 5,093,124, 6,419,941, and 6,756,046, which are herein incorporated by reference. While the fatty acid compound can be present in the composition in a variety of amounts, in an exemplary embodiment, the fatty acid compound active ingredient (e.g., the fatty acid, the fatty acid sugar ester, or the fatty acid salt) may be present at an end use concentration range of about 0.05 percent by weight to 2.0 percent by weight. The combination of a fatty acid compound insecticide and a spinosyn, such as spinosad, is particularly advantageous in that while fatty acid compound insecticides are acute toxins that exhibit no residual activity, spinosyns exhibit residual activity and are ingested toxins.

Moreover, the at least one additional insecticide and/or miticide can be an oil, and the oil can be any oil that can coat the surface of insects or mites, thereby flooding the spiracles causing them to suffocate. The oil can also interact with the fatty acids in the insect membranes interfering with metabolism and acting as a poison, or attack the Octopamine neuroreceptors. Exemplary oils can include plant oil, vegetable oil, mineral oil, and/or essential oil. Exemplary plant oils can include sesame oil, canola oil, cottonseed oil, soybean oil, coconut oil, sunflower oil, safflower oil, rape seed oil, peanut oil, neem oil, olive oil, and mixtures thereof, and exemplary essential oils can include d-limonene, eugenol, cinnamon oil, clove oil, thyme oil, thymol, geraniol, rosemary oil, linalool, mint oil, peppermint oil, citrus oil, garlic oil, pepper oil, and mixtures thereof. In an exemplary embodiment, the oil can be present in the composition at an end use concentration of about 0.05 percent by weight to 5.0 percent by weight. Further exemplary additional insecticides and/or miticides can include salts of vegetable oils such as sunflower oil, safflower oil, canola oil, sesame oil, olive oil, neem oil, coconut oil, cottonseed oil, and blends thereof. Saponified forms of these compounds can include potassium, sodium, and ammonium salts.

The at least one additional insecticide and/or miticide can also be a naturally occurring pyrethrum oil or extract, and exemplary pyrethrum extracts can be obtained from dried flowers such as a chrysanthemum (*Chrysanthemum cinerariaefolium*). The principal parts of the chrysanthemum from which pyrethrum extracts are derived include the achenes, petals, receptacles, scales, and disc florets. By way of non-limiting example, pyrethirum extracts are commercially available from a number of sources, including the Pyrethrum Marketing Board from Kenya, Africa, M.G.K. Company from Minneapolis Minn., Fairfield American Corp. from Rutherford, N.J., and Prentiss Drug and Chemical Co. from Floral Park, N.Y. The active agents of pyrethrum extracts are generally referred to as "pyrethrins," and known pyrethrins can include pyrethrin I, pyrethrin II, cinerin I, cinerin II, jasmolin I, and jasmolin II. The total pyrethrin component of most commercially available pyrethrum extracts generally is in the range of about 15% to 30% by weight, and more commonly, pyrethrum extracts are utilized with a total pyrethrin content in the range of about 20% to 25% by weight. While the pyrethrins can be present in any of the compositions disclosed herein in a variety of concentrations, in an exemplary embodiment, it can be present at an end use concentration in the range of about 10 ppm by weight to 4,000 ppm by weight.

Besides the fatty acid family, plant oils, vegetable oils, and essential oils, mineral (paraffinic) oils can be used as an additional insecticide and/or miticide, and in particular to treat soft bodies aphids and mites. In one embodiment, the mineral oil can coat the surface of the insects or mites thereby flooding the spiracles causing them to suffocate. The mineral oil can also interact with the fatty acids in the insect membranes interfering with metabolism and acting as a poison. Exemplary mineral oils are commercially available under a variety of brands including Sunspray® Ultra-Fine® Spray Oil from Sunoco Inc. of Ten Penn Center, 1801 Market Street Philadelphia, Pa. 19103-1699 and Vegol Growing Season Spray Oils from Lily Miller of P.O. Box 2289, Clackamas, Oreg., USA, 97015. While the oil can be present in the composition in a variety of amounts, in an exemplary embodiment, the oils can be present in end use concentrations ranging from 0.1 percent by weight to 5.0 percent by weight.

Additionally, compounds which kill mites alone, such as avermectins, can be added to the at least one spinosyn to form an insecticidal and miticidal composition. Alternatively, such compounds which kill mites alone can be added to the at least one spinosyn and at least one of an additional insecticide and miticide to form an insecticidal and miticidal composition. Exemplary avermectins can include abamectin, which is produced by Merck & Co. of Rahway, N.J.

The combination of contact insecticides and/or miticides, such as fatty acid salts or oils, with a spinosyn, such as Spinosad, is particularly advantageous in that the combination controls a wide spectrum of insect pests. Contact insecticides effectively control soft-bodied, sucking insects such as insects from the order Homoptera (e.g. aphids, whiteflies, mealybugs, scales) but have limited activity on insect pests from other orders. Spinosad is particularly effective against chewing and biting insects such as insects from the order Lepidoptera (caterpillars), Coleoptera (beetles) and Thysanoptera (thrips) but has limited activity against soft-bodied pests, sucking pests, which are key pests in the home and garden consumer market. Combinations of contact insecticides with Spinosad provide wide spectrum insect and mite control, and synergy (greater than additive effects) are also observed with some combinations, as shown below.

The composition can also include at least one of a solvent and a carrier. The solvent can be any compound that disperses the spinosyn such that the concentration of the spinosyn is decreased without affecting the pesticidal effectiveness thereof. In one exemplary embodiment, the at least one solvent can be any chemical compound whose molecules contain a hydroxyl group bonded to a carbon atom, such as, for example, methanol or ethanol. Alternatively, or in addition, the at least one solvent can be water, propylene glycol, glycerol, ethanol, isopropyl alcohol, methanol, tetrahydrofufuryl alcohol, oils, and combinations thereof. The carrier can be a bait carrier or a dry carrier. Exemplary bait carriers can include a bait that is adapted to draw the pests to the composition such that it can be readily consumed by insects. Exemplary bait carriers can include agar, potato dextrose agar, sugar beet, gelatin, oil cake, pet food, wheat, wheat flour, soya, oats, corn, rice, fruits, fish by-products, sugars, coated vegetable and cereal seeds, casein, whey, blood meal, bone meal, yeast, paper products, natural and synthetic clays such as diatomaceous earth, talc, magnesium aluminum silicates, kaolinites, calcium carbonate, chalk, fats including suet and lard, and a variety of cereals including wheat cereal. In an exemplary embodiment, the bait is a wheat cereal, which is commercially available from, for example, Cargill, Inc. of P.O. Box 9300, Minneapolis, Minn. Exemplary dry carriers can include clays, diatomaceous earth, flours, bran, sand, pumice, sugar, corncob, Biodac (which is produced by Gran-Tec, Green Bay, Wis.), sodium bicarbonate, calcium carbonate, and combinations thereof.

One skilled in the art will appreciate that a variety of other compounds can be added to the insecticidal composition depending upon the needs of the user. In one embodiment surfactants, and preferably non-ionic and amphoteric surfactants, can be useful in the composition to reduce the surface tension of the liquid concentrate or RTU liquid spray to allow more intimate contact between the spray droplet and the plant. Preferred nonionic surfactants include ethoxylated sorbitan derivatives, ethoxylated fatty acids, and mixtures thereof. Exemplary ethoxylated sorbitan derivatives include TWEEN surfactants, such as TWEEN 81 and TWEEN 85, available from ICI Americas, Inc., Agricultural Products Division of Wilmington, Del. Other suitable sorbitan derivatives include EMSORB 6903 and EMSORB 6913, available from Henkel Corp. of Cincinnati, Ohio. Suitable ethoxylated fatty acids include CHEMAX T09 and CHEMAX E400MO available from Chemax, Inc. of Greenville, S.C., and ALKASURF 014 and ALKASURF 09, available from Rhone Poulenc of Cranberry, N.J. Preferred amphoteric surfactants include cetyl (C16) betaine, known chemically as 1-hexadecanaminium, N-(carboxymethyl)N,N-dimethyl-, inner salt (CAS number 693-334) available, from Deforest Enterprises FL, USA.

In another embodiment, antioxidants can be added to the composition in order to reduce the effect of oxidation of the composition. Examples of suitable antioxidants include butylated hydroxytoluene (BHT), butylated hydroxy anisole (BHA), alpha-tochopherol, ethoxyquin (6-ethoxy-2,2,4-trimethyl-1,2-dihydroquinoline), and 2,6-dioctadecyl-P-cresol (DOPC). Alternatively, additional additives, such as stabilizers, can be added to improve the stability and shelf life of the composition. Examples of suitable additives include gum arabic, guar gum, sodium caseinate, polyvinyl alcohol, locust bean gum, xanthan gum, kelgum, and mixtures thereof.

While exemplary compositions, such as those discussed above, are in the form of a liquid concentrate or RTU liquid spray, one skilled in the art will appreciate that the compositions can also be in a dust or a solid form. While the solid form can be any solid composition that can be spread on or around areas infested by insects and/or mites as well as in areas to prevent infestation of insects and/or mites, exemplary solid compositions are in the form of powders, granules, cubes, or pellets.

One skilled in the art will appreciate that the insecticidal/miticidal composition can also include additional formulation enhancing additives, such as preservatives or anti-microbial agents, phagostimulants, waterproofing agents, taste altering additives, or any combination thereof.

A variety of preservatives can be used effectively with the insecticidal/miticidal composition of the present invention, and exemplary preservatives include Legend MK® available from Rohm & Haas Company of Philadelphia, Pa., and CA-24 available from Dr. Lehmann and Co. of Memmingen/ Allgäu, Germany. While the preservatives can be present in the composition in a variety of amounts, preferably the preservatives, such as those listed above for example, can be mixed with water to form a stock solution to be added to the formulation at a concentration in the range of about 1 ppm to 750 ppm.

Phagostimulants can be added to the composition to attract insects and to induce them to feed upon the composition. A variety of phagostimulants can be used, including sugars, yeast products, and casein, and in an exemplary embodiment sugars, such as sucrose, are used. These additives are normally incorporated within the composition in a dry form in a variety of amounts, however typically, they can be added to the composition at about 1 percent by weight to 2.5 percent by weight of the total composition.

Waterproofing agents, which can also act as binders, can also be added to the composition to improve the composition's weatherability. These are typically water insoluble compounds such as waxy materials and other hydrocarbons. Examples of suitable waterproofing agents are paraffin wax, stearate salts, beeswax, and similar compounds. One preferred wax compound is PAROWAX®, available from Conros Corp. of Scarborough, Ontario, Canada. Waterproofing agents can be incorporated into the composition in dry form in a variety of amounts, however in an exemplary embodiment waterproofing agents are incorporated into the composition at about 5 percent by weight to 12 percent by weight of the total composition.

The composition can also include a taste altering compound to render the composition unpalatable to animals. Exemplary compositions include those having a bitter taste, and suitable compounds that are commercially available include BITREX, available from McFarlane Smith Ltd. of Edinburgh, Scotland. These compounds typically are added at very low concentrations, and, for example, a 0.1% BITREX solution can typically be added to the composition at about 1 percent by weight to 2 percent by weight of the total composition.

Methods for controlling insect and mite pests are also provided. In one embodiment, a method can include providing a composition that has an effective amount of at least one spinosyn, at least one of an additional insecticide and miticide, and at least one of a solvent or a carrier, and administering an effective amount of the composition to control pests. Where the composition is a liquid, the method can further include administering an effective amount of the composition such that an effective amount of the composition contacts pests, plants and plant products, the vicinity of the pests, and/or the vicinity of the plants and plant products. In another embodiment, where the composition is a dust or a solid, administering an effective amount of the composition can include placing an effective amount of the composition in a vicinity of pests and/or placing an effective amount of the composition in a vicinity of plants and plant products to be protected.

The following non-limiting examples serve to further describe the invention. In all of the examples, the percent of the active ingredient is on a weight percent basis.

Example 1

Test of Spinosad Combinations to Control Green Peach Aphids

The purpose of this test was to evaluate spinosad combined with a fatty acid salt insecticide for controlling green peach aphids, which can commonly be found on radish plants. Following formation of compositions of spinosad using the commercially available form of spinosyn Gardens Alive Bulls-Eye™ as well as the fatty acid salt Neudosan™ (having potassium salt of fatty acids as the active ingredient), green peach aphids were brushed from radish plants in a laboratory colony onto plate glass for treatment. Each replicate was sprayed with one spray from a hand-held trigger sprayer using the liquid compositions noted in the table below. After 90 seconds, treated aphids were transferred into filter paper lined petri plates using a fine camelhair brush. Each treatment consisted of 10 replicates of 10 aphids each, and mortality was assessed after 1 day.

Table 1, below, illustrates the results obtained from compositions of Spinosad, fatty acid salt, and combinations thereof.

TABLE 1

Effect of compositions of Spinosad, fatty acid salt, and spinosad and fatty acid salt combinations on the mortality of green peach aphids.

| Compound | Observed Mean % Mortality (after 1 day) | Expected Mean % Mortality (after 1 day) |
| --- | --- | --- |
| Spinosad (50 ppm ai) - Gardens Alive Bulls-Eye ™ Bioinsecticide | 10.0 | N/A |
| Spinosad (200 ppm ai) - Gardens Alive Bulls-Eye ™ Bioinsecticide | 11.0 | N/A |
| Neudosan ™ (1.0% ai fatty acid salts) | 71.0 | N/A |
| 50 ppm ai Spinosad + 1.0% ai fatty acid salts (Neudosan) | 86.0 | 81.0 |
| 200 ppm ai Spinosad + 1.0% ai fatty acid salts (Neudosan) | 81.0 | 82.0 |
| Deionized Water | 9.0 | N/A |

Example 2

Test of Spinosad Combinations to Control Green Peach Aphids

The purpose of this test was to evaluate spinosad in combination with fatty acid salts or vegetable oil for controlling green peach aphids, which can commonly be found on radish plants. Spinosad-based compositions using the commercially available form of spinosyn SpinTor™, the fatty acid salt Neudosan™, and an oil (Vegol Growing Season Spray Oil®) were formed, and tested similar to that as described with respect to Table 1.

Table 2, below, illustrates the results obtained from compositions of spinosad, fatty acid salt, oil, and combinations thereof.

TABLE 2

Effect of compositions of Spinosad, fatty acid salt, oil, and spinosad, fatty acid salt, and oil combinations on the mortality of green peach aphids.

| Compound | Observed Mean % Mortality (after 1 day) | Expected Mean % Mortality (after 1 day) |
| --- | --- | --- |
| Spinosad (50 ppm ai) - SpinTor ™ | 9.0 | N/A |
| Spinosad (200 ppm ai) - SpinTor ™ | 6.0 | N/A |
| Neudosan ™ (0.5% ai fatty acid salts) | 15.0 | N/A |
| 50 ppm ai Spinosad SpinTor ™ + 0.5% ai fatty acid salts (Neudosan ™) | 25.0 | 24.0 |
| 200 ppm ai Spinosad SpinTor ™ + 0.5% ai fatty acid salts (Neudosan ™) | 38.0 | 21.0 |

TABLE 2-continued

Effect of compositions of Spinosad, fatty acid salt, oil, and spinosad, fatty acid salt, and oil combinations on the mortality of green peach aphids.

| Compound | Observed Mean % Mortality (after 1 day) | Expected Mean % Mortality (after 1 day) |
| --- | --- | --- |
| Vegol Growing Season Spray Oil ® (1.0% ai canola oil) | 56.0 | N/A |
| 50 ppm ai Spinosad SpinTor ™ + 1.0% ai (canola oil). Vegol Growing Season Spray Oil ® | 65.0 | 65.0 |
| 200 ppm ai Spinosad SpinTor ™ + 1.0% ai (canola oil) Vegol Growing Season Spray Oil ® | 75.0 | 62.0 |
| Deionized Water | 5.0 | N/A |

Example 3

Test of Spinosad Combinations to Control Green Peach Aphids

The purpose of this test was to evaluate spinosad in combination with Canola oil for controlling green peach aphids, which can commonly be found on radish plants. Spinosad-based compositions using the commercially available form of spinosyn SpinTor™ as well as the oil Vegol Growing Season Spray Oil® were formed, and tested similar to that as described with respect to Table 1.

Table 3, below, illustrates the results obtained from compositions of spinosad, oil, and combinations thereof.

TABLE 3

Effect of compositions of Spinosad, oil, and spinosad and oil combinations on the mortality of green peach aphids.

| Compound | Observed Mean % Mortality (after 1 day) | Expected Mean % Mortality (after 1 day) |
| --- | --- | --- |
| Vegol Growing Season Spray Oil ® (1.5% ai canola oil) | 69.0 | N/A |
| Spinosad (50 ppm ai) - SpinTor ™ | 6.0 | N/A |
| Spinosad (200 ppm ai) - SpinTor ™ | 9.0 | N/A |
| Spinosad (1000 ppm ai) - SpinTor ™ | 10.0 | N/A |
| 50 ppm ai Spinosad SpinTor ™ + 1.5% ai (Canola oil) Vegol Growing Season Spray Oil ® | 82.0 | 75.0 |
| 200 ppm ai Spinosad SpinTor ™ + 1.5% ai (Canola oil) Vegol Growing Season Spray Oil ® | 70.0 | 78.0 |
| 1000 ppm ai Spinosad SpinTor ™ + 1.5% ai (Canola oil) Vegol Growing Season Spray Oil ® | 89.0 | 79.0 |
| Deionized Water | 3.0 | N/A |

Example 4

Test of Spinosad Combinations to Control Green Peach Aphids

The purpose of this test was to evaluate spinosad in combination with fatty acid salts for controlling green peach aphids, which can commonly be found on radish plants. Spinosad-based compositions using the commercially available form of spinosyn SpinTor™ as well as the fatty acid salt Neudosan™ were formed, and tested similar to that as described with respect to Table 1.

Table 4, below, illustrates the results obtained from compositions of spinosad, fatty acid salt, and combinations thereof.

TABLE 4

Effect of compositions of Spinosad, fatty acid salt, and spinosad and fatty acid salt combinations on the mortality of green peach aphids.

| Compound | Observed Mean % Mortality (after 1 day) | Expected Mean % Mortality (after 1 day) |
|---|---|---|
| Spinosad (1000 ppm ai) - SpinTor ™ | 7.0 | N/A |
| 0.25% ai fatty acid salts (Neudosan ™) | 12.0 | N/A |
| 0.5% ai fatty acid salts (Neudosan ™) | 30.0 | N/A |
| 1.0% ai fatty acid salts (Neudosan ™) | 65.0 | N/A |
| 1000 ppm ai Spinosad SpinTor ™ + 0.25% ai fatty acid salts (Neudosan ™) | 39.0 | 19.0 |
| 1000 ppm ai Spinosad SpinTor ™ + 0.5% ai fatty acid salts (Neudosan ™) | 77.0 | 37.0 |
| 1000 ppm ai Spinosad SpinTor ™ + 1.0% ai fatty acid salts (Neudosan ™) | 90.0 | 72.0 |
| Deionized Water | 4.0 | N/A |

Example 5

Test of Spinosad Combinations to Control Adult House Flies

The purpose of this test was to evaluate spinosad in combination with fatty acid salts for controlling adult house flies. Following the formation of Spinosad-based compositions using the commercially available form of spinosyn SpinTor™ as well as the fatty acid salt Neudosan™, adult house flies from a laboratory colony were anaesthetized with $CO_2$ and placed onto six inch round styrofoam plates for treatment with two sprays from a hand-held trigger sprayer using the liquid compositions noted in Table 5. After treatment, the flies were placed onto paper towel lined styrofoam plates and then transferred to 250 mL clear plastic cups containing a small amount of granulated sugar and a water reservoir covered with netting. The treatments consisted of 8 replicates of 5 flies each, and mortality was assessed after 4 hours.

Table 5, below, illustrates the results obtained from compositions of spinosad, fatty acid salt, and combinations thereof.

TABLE 5

Effect of compositions of Spinosad, fatty acid salt, and spinosad and fatty acid salt combinations on the mortality of adult house flies.

| Compound | Observed Mean % Mortality (after 4 hours) | Expected Mean % Mortality (after 4 hours) |
|---|---|---|
| 0.5% ai fatty acid salts (Neudosan ™) | 50.0 | N/A |
| Spinosad (50 ppm ai) - SpinTor ™ | 17.5 | N/A |
| Spinosad (500 ppm ai) - SpinTor ™ | 62.5 | N/A |
| 50 ppm ai Spinosad SpinTor ™ + 0.5% ai fatty acid salts (Neudosan ™) | 95.0 | 67.5 |
| 500 ppm ai Spinosad SpinTor ™ + 0.5% ai fatty acid salts (Neudosan ™) | 100.0 | 100.0 |
| Deionized Water | 0.0 | N/A |

Example 6

Test of Spinosad Combinations to Control Western Tent Caterpillar Larvae

The purpose of this test was to evaluate spinosad in combination with fatty acid salts for controlling Western tent caterpillar larvae. Following the formation of Spinosad-based compositions using the commercially available form of spinosyn SpinTor™ as well as the fatty acid salt Neudosan™, western tent caterpillar larvae were collected from infested trees outdoors and placed onto six inch round styrofoam plates for treatment with two sprays from a hand-held trigger sprayer using the liquid compositions noted in Table 6. After treatment, the larvae were placed onto paper towel lined styrofoam plates and then transferred into filter paper lined Petri dishes. The treatments consisted of 8 replicates of 5 larvae each, and mortality was assessed after 1 day.

Table 6, below, illustrates the results obtained from compositions of spinosad, fatty acid salt, and combinations thereof.

TABLE 6

Effect of compositions of Spinosad, fatty acid salt, and spinosad and fatty acid salt combinations on the mortality of Western tent caterpillar larvae.

| Compound | Mean % Mortality (after 1 day) |
|---|---|
| 0.5% ai fatty acid salts (Neudosan ™) | 35.0 |
| Spinosad (50 ppm ai) SpinTor ™ | 80.0 |
| Spinosad (200 ppm ai) SpinTor ™ | 80.0 |
| 0.5% ai fatty acid salts (Neudosan ™) + Spinosad (50 ppm ai) SpinTor ™ | 90.0 |
| 0.5% ai fatty acid salts (Neudosan ™) + Spinosad (200 ppm ai) SpinTor ™ | 95.0 |
| Deionized water | 2.5 |

Example 7

Test of Spinosad and Pyrethrum Extract Combination to Control Ants

The purpose of this test was to evaluate Spinosad in combination with pyrethrum extract for controlling odorous house ants. Following the formation of Spinosad-based compositions using the commercially available form of spinosyn Entrust™, ants were placed into tubs. Each tub included a sugar bait as noted in Table 7. The sides of tubs were covered with Vaseline to prevent escapes and the tubs were covered with screened lids. Each treatment consisted of 4 replicates of 5 ants each, and mortality was assessed after 1 and 4 days.

Table 7, below, illustrates the results obtained from compositions of Spinosad, pyrethrum extract, and combinations thereof.

TABLE 7

Effect of compositions of Spinosad, pyrethrum extract and Spinosad and pyrethrum extract combinations on the mortality of odorous house ants.

| Compound | Mean % Mortality (after 1 day) |
|---|---|
| Pyrethrum Extract (1750 ppm ai) | 45.0 |
| Spinosad (250 ppm ai) Entrust ™ | 20.0 |

TABLE 7-continued

Effect of compositions of Spinosad, pyrethrum extract and Spinosad and pyrethrum extract combinations on the mortality of odorous house ants.

| Compound | Mean % Mortality (after 1 day) |
|---|---|
| Pyrethrum extract + Spinosad (250 ppm ai) Entrust ™ | 90.0 |
| Untreated | 0.0 |

Example 8

Test of Spinosad Combinations to Control Mites

The purpose of this test was to evaluate Spinosad in combination with Neudosan™ (fatty acid salts) for residual control of twospotted spider mites. Spinosad-based compositions were formulated using the commercially available form of Spinosad SpinTor™ as well as the fatty acid salt Neudosan™. Bean plants were trimmed to two primary leaves and both the top and bottom leaf surfaces were treated with compositions noted in Table 8. One day later, when plants were dry, adult female twospotted spider mites were placed on each plant at about 25 mites per plant. Treatments consisted of 10 replicates of one plant each, and mortality and population levels were assessed 7 days following mite introduction.

Table 8 below, illustrates the results obtained from compositions of Spinosad, fatty acid salts, and combinations thereof.

TABLE 8

Effect of compositions of Spinosad, fatty acid salts, and Spinosad and fatty acid salts combinations on twospotted spider mites.

| Compound | Mean % Mortality | Average Number of Live Adults (after 7 days) | Average Number of Live Nymphs (after 7 days) |
|---|---|---|---|
| Spinosad (50 ppm ai) - SpinTor ™ | 24.0 | 11.8 | 37.8 |
| Spinosad (200 ppm ai) - SpinTor ™ | 51.6 | 5.7 | 39.0 |
| 1.0% ai fatty acid salts (Neudosan ™) | 22.6 | 13.2 | 35.0 |
| 50 ppm ai Spinosad SpinTor ™ + 1.0% ai fatty acid salts (Neudosan ™) | 52.8 | 1.4 | 12.8 |
| 200 ppm ai Spinosad SpinTor ™ + 1.0% ai fatty acid salts (Neudosan ™) | 88.9 | 0.4 | 0.0 |
| Deionized Water | 15.7 | 16.2 | 48.0 |

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for the control of insect and mite pests, comprising: providing a composition having at least one spinosyn present at an end use concentration in the range of about 1 ppm to 20,000 ppm,
   at least one of an additional insecticide and miticide comprising a fatty acid salt, the at least one of an additional insecticide and miticide being present at an end use concentration in the range of about 0.05 percent by weight to 2.0 percent by weight, and
   at least one of a solvent and a carrier; and
   administering an effective amount of the composition by contacting plants and/or plant products or contacting a vicinity of the plants and/or plant products to control pests.

2. The method of claim 1, wherein the composition is a liquid and administering an effective amount of the composition includes at least one of contacting pests, contacting plants and plant products, contacting a vicinity of the pests, and contacting a vicinity of the plants and plant products with an effective amount of the composition.

3. The method of claim 1, wherein the composition is a solid and administering an effective amount of the composition includes at least one of placing an effective amount of the composition in a vicinity of pests and placing an effective amount of the composition in a vicinity of plants and plant products to be protected.

4. The method of claim 1, wherein the composition is a dust and administering an effective amount of the composition includes at least one of placing an effective amount of the composition in a vicinity of pests and placing an effective amount of the composition in a vicinity of plants and plant products to be protected.

5. The method of claim 1, wherein the fatty acid salt is selected from the group consisting of potassium, sodium, and ammonium fatty acid salts of saturated or unsaturated fatty acids with carbon chain lengths ranging from C8 to C18.

6. The method of claim 1, wherein the solvent is selected from the group consisting of water, glycerol, propylene glycol, ethanol, isopropyl alcohol, methanol, tetrahydrofurfuryl alcohol, oils, and combinations thereof.

7. The method of claim 1, further comprising a formulation enhancing additive selected from the group consisting of preservatives, anti-microbial agents, phagostimulants, waterproofing agents, taste altering additives, and combinations thereof.

8. The method of claim 1, wherein the carrier is a bait carrier.

9. The method of claim 1, wherein the carrier is a dust carrier.

* * * * *